US005756872A

United States Patent [19]
Smith, Jr. et al.

[11] Patent Number: 5,756,872
[45] Date of Patent: May 26, 1998

[54] PROCESS FOR THE TREATMENT OF FCCU OFF GAS

[75] Inventors: Lawrence A. Smith, Jr.; John R. Adams, both of Pasadena, Tex.

[73] Assignee: Catalytic Distillation Technologies, Pasadena, Tex.

[21] Appl. No.: 789,650

[22] Filed: Jan. 27, 1997

[51] Int. Cl.$^6$ .............. C07C 2/70; C07C 2/66; C07C 7/148

[52] U.S. Cl. .......... 585/449; 585/323; 585/448; 585/466; 585/467; 585/809

[58] Field of Search .................. 585/312, 314, 585/323, 448, 449, 466, 467, 809

[56] References Cited

U.S. PATENT DOCUMENTS

| | | | |
|---|---|---|---|
| 1,994,249 | 3/1935 | Ipatieff et al. | 260/168 |
| 2,860,173 | 11/1958 | Jones et al. | 260/671 |
| 4,140,622 | 2/1979 | Herout et al. | 208/93 |
| 4,358,362 | 11/1982 | Smith et al. | 208/91 |
| 4,387,259 | 6/1983 | Barile | 585/467 |
| 5,043,506 | 8/1991 | Crossland | 585/449 |
| 5,082,990 | 1/1992 | Hsieh et al. | 585/467 |
| 5,243,115 | 9/1993 | Smith, Jr. et al. | 585/446 |
| 5,446,223 | 8/1995 | Smith, Jr. | 585/313 |

OTHER PUBLICATIONS

Survey of Industrial Chemistry, 2 nd revised edition; Chenier; pp. 130–133, 1992.

*Primary Examiner*—Glenn Caldarola
*Assistant Examiner*—Thuan D. Dang
*Attorney, Agent, or Firm*—Kenneth H. Johnson

[57] ABSTRACT

A process wherein an FCCU off gas is treated by first subjecting the off gas to an alkylation with a heavy reformat to remove the propylene and contaminants after which the gas is separated from the reformat and alkylated products by distillation to produce an ethylene feed suitable for the reaction with benzene to produce ethyl benzene.

11 Claims, 1 Drawing Sheet

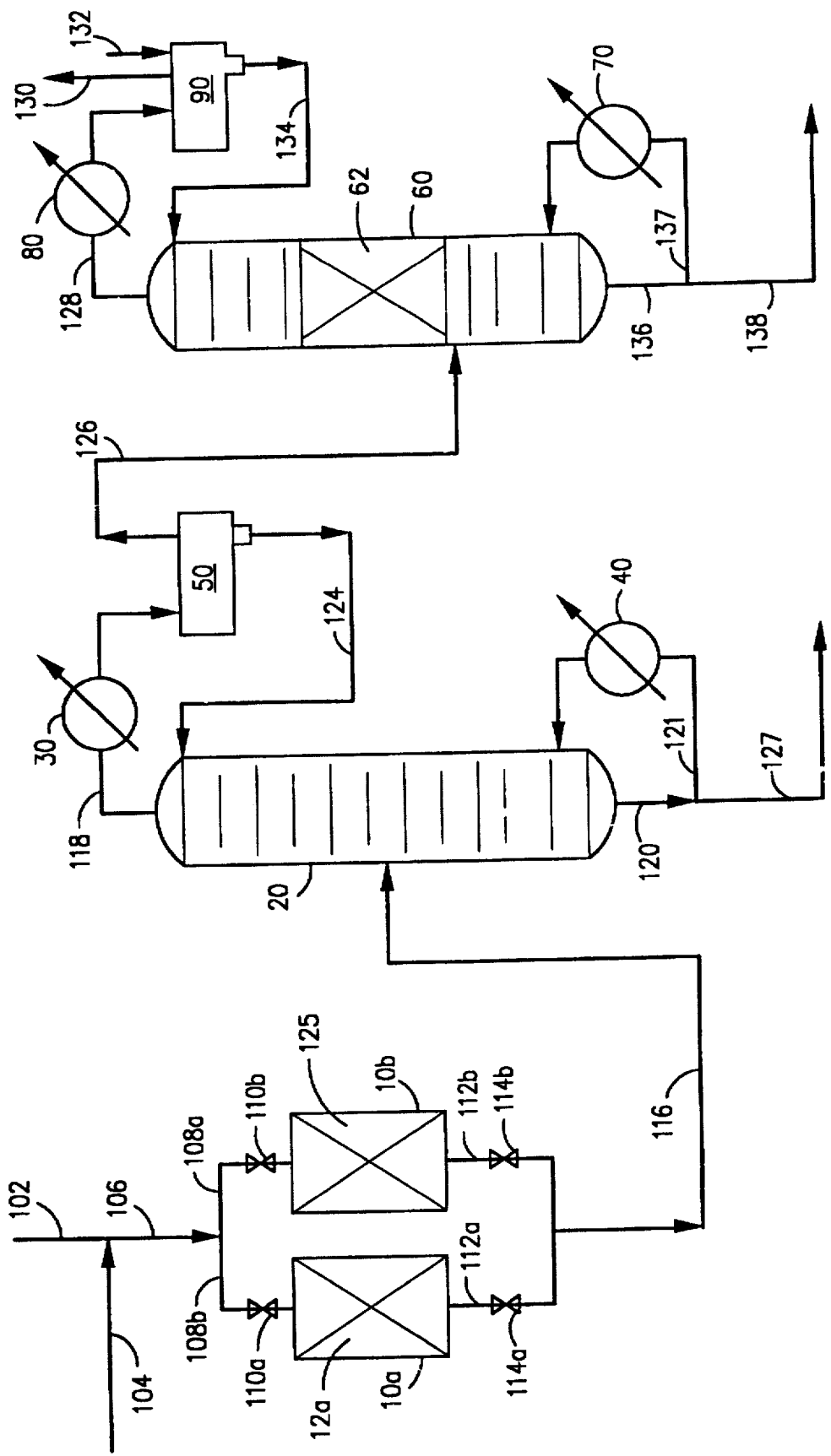

PROCESS FOR THE TREATMENT OF FCCU OFF GAS

BACKGROUND OF THE INVENTION

1. Field of the Invention

The present invention relates to the production of ethyl benzene utilizing the ethylene in an FCCU off gas stream. More particularly, the process relates to a process for treating an FCCU off gas stream containing ethylene to remove catalyst poisons and selectively react the propylene contained in the stream.

2. Related Information

Ethyl benzene and cumene have traditionally been produced by the reaction of benzene and the respective olefin, i.e., ethylene and propylene in the presence of an acidic catalyst. In some known processes the catalyst is highly corrosive and has a relatively short life, e.g., $AlCl_3$, $H_3PO_4$ on clay, $BF_3$ on alumina, and others require periodic regeneration, e.g., molecular sieves. The exothermicity of the reaction and the tendency to produce polysubstituted benzene require low benzene conversions per pass with large volume recycle in conventional processes.

To overcome many of the disadvantages of the conventional processes, a process has been developed wherein the reaction of the olefin with benzene is carried out concurrently with separation of the products by fractional distillation. One embodiment of that process is disclosed in U.S. Pat. No. 5,243,115.

In addition the use of an FCCU off gas stream in the alkylation of the organic aromatics contained in a reformat stream is disclosed in U.S. Pat. No. 5,082,990. The reference particularly describes the concurrent reaction and distillation of U.S. Pat. No. 5,243,115.

In fluid catalytic cracking a heavy "gas oil" stream having a boiling range circa 600°–1200° F. is combined with a fine catalytic substance, usually a zeolitic material, at elevated temperatures, usually above 900° F., which breaks apart or cracks the longer chain hydrocarbons to shorter chain hydrocarbons. In the absence of hydrogen (and suitable hydrogenation pressures) some unsaturated compounds are produced. Some gas is produced, the amount depending on the severity of the cracking, the gas also being rich in unsaturated compounds, i.e., ethylene, propenes, and butenes. Since the compounds have value, they are usually recovered and used or sold separately. However, the unsaturated compound or olefin separation results in "waste gas" having an olefin content of up to 20 mole percent. This waste gas is normally used as fuel in the refinery heaters.

A typical FCCU off gas contains $C_2$ to $C_4$ olefins (mostly ethylene and propylene), some saturated compounds, nitrogen compounds such as ammonia, carbon monoxide and water. The latter compounds are catalyst poisons for the molecular sieves used in the alkylation process. In addition the propylene preferentially reacts with benzene to form cumene which, in an ethyl benzene process requires separation.

The major drawback of using the combined reaction distillation process for the alkylation of reformat with an FCCU off gas is that the catalyst is deactivated fairly quickly due to the poisons. In a distillation column reactor the replacement or regeneration of the catalyst is difficult.

SUMMARY OF THE INVENTION

The present invention utilizes a two phase fixed bed down flow reactor (guard bed reactor) to react the propylene in an FCCU off gas stream with the aromatics, primarily benzene, in a refinery reformat stream and adsorb the poisons in the FCCU off gas stream. The effluent from the reactor is fed to a distillation column where gasoline ($C_7$ and heavier) is taken as bottoms and $C_6$ and lighter material is taken as overheads. The overheads contain the purified gas and perhaps some benzene which may be fed to an ethyl benzene production unit. These overheads are particularly useful in a dilute ethyl benzene process wherein the ethylene is fed in a very dilute gas to a distillation column reactor.

The catalyst in the guard bed reactor preferably reacts only propylene with the aromatics. One such catalyst is the family known as solid phosphoric acid (SPA) catalysts which can specifically react the propylene and leave the ethylene. Other useful catalysts are the common acid molecular sieves which will preferentially react the propylene in a mixture with ethylene. If desired the SPA catalyst can be combined in the bed with a common molecular sieve which will preferentially absorb the catalyst poisons in the gas stream.

BRIEF DESCRIPTION OF THE DRAWING

The FIGURE is a flow diagram of a process utilizing the invention in an integrated ethyl benzene process.

DETAILED DESCRIPTION OF THE INVENTION

One aspect of the invention is a process for the removal of propylene from a refinery gas stream containing ethylene and propylene, comprising passing the gas stream and a liquid stream containing organic aromatic compounds over a fixed bed of an alkylation catalyst which preferentially reacts the propylene with organic aromatic compounds and fractionates the effluent from the fixed bed to separate the remaining gas from the liquid stream. Another aspect of the invention is a process for the production of ethylbenzene utilizing an FCCU off gas containing ethylene, propylene, water, carbon oxides, nitrogen compounds and inert alkanes.

The FCCU waste gas contains a variety of unrecovered olefins, however the preponderant olefinic compounds are ethylene, propylene (propenes) and butenes. The remainder of the gas is made up of various saturated hydrocarbons. Table I below gives an analysis of a typical waste gas for use in the invention. The analysis was performed by gas chromatography and the components are given as weight percent.

TABLE I

Typical Gas Analysis

| Component | wt. % |
|---|---|
| $C_{1-}$ | 21.1 |
| $C_2$ | 11.1 |
| $C_{2-}$ | 12.7 |
| $C_3$ | 30.6 |
| $C_{3-}$ | 7.9 |
| $C_4$ | 0.4 |
| $C_4$ | 0.7 |
| $C_5^+$ | 0.1 |
| $N_2$ | 13.5 |
| $H_2$ | 1.7 |
| $CO_2$ | 0.3 |

As may be seen from the analysis of the waste gas the typical total olefin content is 42.1 percent, divided into ethylene, 11.1 percent; propene, 30.6 percent; and butenes and higher, 0.4 percent. The nitrogen in the table is total nitrogen and comprises ammonia or any assortment of amines and/or amides.

In catalytic reforming, the raw naphtha, having a boiling range of circa 115°–350° F., is passed over an alumina supported noble metal catalyst at elevated temperatures (circa 920°–950° F.) and moderate pressure (circa 200–550 psig). The catalyst "reforms" the molecular structures of the hydrocarbons contained in the raw naphtha by removing hydrogen and rearranging the structure of the molecules so as to improve the octane number of the naphtha. However, the increase in octane number also reduces the liquid volume of the naphtha as the specific gravity is increased.

Because of the multiplicity of the compounds in the raw naphtha, the actual reactions which occur in catalytic reforming are numerous. However, some of the many resulting products are aryl or aromatic compounds, all of which exhibit high octane numbers. The aryl compounds produced depend upon the starting materials which in a refinery are controlled by the boiling range of the naphtha used and the crude oil source. The "reformed" product from a catalytic reforming process is commonly called reformat and is often separated into two fractions by conventional distillations—a light reformat having a boiling range of circa 115°–250° F. and a heavy reformat having a boiling range of circa 250°–400° F. The aryl compounds in each fraction are thus dependent upon their boiling points. The lower boiling or lighter aryl compounds, e.g., benzene, toluene and xylenes, are contained in the light reformat, and higher boiling aryl compounds are contained in the heavy reformat.

The reformat used in the instant invention is preferably a heavy reformat to facilitate the separation of the purified gas from the gasoline. If either a light or full range reformat stream is used, the distillation column used for separation is preferably operated to take a $C_6$ and lighter cut overhead with the bottoms containing the $C_7$ and heavier material including toluene and xylenes which would react with the ethylene and produce a mixture which would be difficult to separate from the ethyl benzene.

Referring now to the FIGURE there is shown a simplified flow diagram of an integrated ethyl benzene process utilizing the present invention.

The FCCU off gas is fed via flow line 104 and is combined in flow line 106 with reformat fed (or any other aromatic rich stream) via flow line 102. Two swing reactors 10a and 10b are fed alternatingly via either flow line 108a or 108b through either valve 110a or 110b. Each reactor contains a bed 12a or 12b of a catalyst selected for its ability to selectively react propylene with the aromatic contained in the reformat stream. Additionally the catalyst beds absorb essentially all of the contaminants contained within the FCCU off gas. The swing reactors are preferred because one catalyst bed can either be replaced or regenerated while the other is in service. Exit from the swing reactors 10a or 10b is through flow line 112a or 112b respectively through either valve 114a or 114b. It should be understood that when valves 110a and 114a are open valves 110b and 114b are closed and vice versa.

The effluent from the reactors less the contaminants and the propylene which has been reacted with aromatics in the reformat is then fed via flow line 116 to a distillation column 20 where the treated gas is separated from the gasoline boiling range reformat. The treated gas is taken as overheads via flow line 118 and partially condensed in condenser 30. The liquids in the overheads are collected and separated from the uncondensed gases in receiver/separator 50. The liquid from the receiver/separator 50 is returned to the column as reflux via flow line 124. If desired some overhead product may also be taken. The gasoline boiling range reformat is taken as bottoms via flow lines 120 and 122. A portion of the bottoms is circulated through reboiler 40 via flow line 121 to provide heat for the distillation column 20. The remainder is sent to gasoline blending via 127.

The overheads, containing the now treated off gas, can be used as feed to an ethyl benzene process. The gas, containing ethylene and essentially inert alkanes, is fed via flow line 126 to a distillation column reactor 60 which contains a bed 62 of suitable alkylation catalyst in the form of a catalytic distillation structure as has been described in U.S. Pat. Nos. 4,443,559; 4,215,011 and 4,302,356 which are incorporated herein in their entirety. The catalyst packing is preferably arranged in the middle portion of the distillation column reactor. The gas is fed below the bed 62.

Benzene is fed to the distillation column reactor 60 conveniently into the reflux drum 90 via flow line 132. In the distillation column reactor 60 essentially all of the ethylene is reacted with an excess of benzene to form ethyl benzene. The dilute ethylene in combination with the excess benzene limits the selectivity to essentially ethyl benzene (EB). The ethyl benzene being the highest boiling component is removed as bottoms via flow line 136 and 138. A portion of the ethyl benzene may be circulated through reboiler 70 via flow line 137 to provide additional heat to the process. Unreacted benzene and inert gases are removed as overheads via flow line 128 with the benzene being condensed in partial condenser 80 and collected in reflux drum 90. The unreacted inert gases are separated from the benzene in the reflux drum 90 and removed via flow line 130. Condensed benzene in the reflux drum is returned to the distillation column reactor 60 as reflux via flow line 134.

The catalyst used in the distillation column bed 62 may be an acid molecular sieve such as the zeolites or an acid cation exchange resin. Most preferably for ethyl benzene production a zeolite beta molecular sieve has been found to be desirable. A catalytic distillation structure for use herein comprises placing particulate catalyst, e.g., the mole sieve or cation exchange resin particles into a plurality of pockets in a cloth belt, which is supported in the distillation column reactor by open mesh, knitted stainless steel wire by twisting the two together in a helical form. This allows the requisite flows and prevents loss of catalyst. The cloth may be any material which is inert in the reaction. Cotton or linen is useful, but fiberglass cloth or "Teflon" cloth is preferred.

The catalyst in the reactors 10a and 10b is a catalyst that preferentially reacts propylene with organic aromatic compounds leaving the ethylene. One such catalyst is the family of catalysts known as solid phosphoric acid catalysts (SPA). The standard acid molecular sieves such as zeolites will suffice but there will be a loss of ethylene. The propylene reacts twenty times as fast as the ethylene over the molecular sieves, but reaction times that ensure complete reaction of the propylene will also allow some of the ethylene to react. In order to absorb the other contaminants (water, CO, nitrogen compounds) in the gas stream, it is preferable to mix in some molecular sieves to remove these contaminants. Preferably less than 50 wt. % of the catalysts in the guard bed reactors is a molecular sieve, more preferably from about 5 to 30 wt. %. There may be more than two guard beds and the composition of the SPA, molecular sieve and/or mixtures there of may be different in the reactors. The SPA and molecular sieve can be intermixed in layers or intimately mixed into a uniform composition or in two distinct layers. Preferably the molecular sieve is downstream such that a substantial portion of the propylene is previously preferentially reacted with the aromatics.

It has been found that zeolites are highly selective for the reaction of propylene with aromatics in the presence of ethylene at temperatures in the range of 150° F. to 225° F. Higher temperatures favor the reaction of ethylene. Lower temperatures substantially reduce the conversion of both ethylene and propylene. In the preferred temperature range the residence time is not a critical factor although at higher temperatures shorter residence time is preferable and at a lower temperature longer residence time is preferable. The preferable range of flow is between 3 and 26 $hr^{-1}$ WHSV in the preferred temperature range.

EXAMPLE

A bench scale down-flow reactor consisting of a ⅝"×6" stainless steel tube packed with 8 g. of catalyst was used to treat a feed containing 90% ethylene, 5% ethane and 5% propylene bubbled into benzene then into the reactor. Typical concentrations in the feed were about 4% ethylene and 0.2–0.5% propylene. The catalyst was LYZ-84. The conditions and results are set out in Table II.

4. The process according to claim 3 wherein said liquid stream comprises a heavy reformat stream.

5. The process according to claim 1 wherein said refinery gas stream comprises an FCCU off gas.

6. A process for the production of ethylbenzene utilizing an FCCU off gas containing ethylene, propylene, water, carbon oxides, nitrogen compounds and inert alkanes comprising the steps of:

(a) feeding the FCCU off gas stream and a reformat stream to a reactor containing a first fixed bed of a solid phosphoric acid catalyst and an acid molecular sieve thereby
  (i) reacting substantially all of the propylene with organic aromatic compounds contained in said heavy reformate stream to produce a product stream containing alkylated aromatic products and
  (ii) absorbing substantially all of said water, carbon oxides and nitrogen compounds onto said catalyst to produce an effluent substantially free of propylene, water, carbon oxides and nitrogen compounds;

TABLE II

| DATE | RUN HOUR | RUN NO. | TEMP °F. | PRES- SURE PSIG | FEED RATE ml/hr | ETH- ENE | ETH- ANE | PRO- PENE | BEN- ZENE | ETHYL- BENZENE | CUMENE | % CONVERSION ETH- ENE | PRO- PENE | WHSV |
|---|---|---|---|---|---|---|---|---|---|---|---|---|---|---|
| 11/16 | 6 | FEED | | | | 1.9422 | 0.1152 | 0.2888 | 97.5982 | 0.0000 | 0.0167 | | | |
| 11/16 | 6 | 1A | 300 | 200 | 120 | 0.0167 | 0.1661 | 0.0022 | 90.1567 | 0.0000 | 0.6469 | 99.4 | 99.5 | 13 |
| 11/17 | 25 | 1A | 300 | 200 | 120 | 0.0333 | 0.1634 | 0.0000 | 89.9802 | 6.6580 | 1.4974 | 98.8 | 100.0 | 13 |
| 11/17 | 28 | 1A | 300 | 200 | 120 | 0.0185 | 0.1503 | 0.0000 | 90.4335 | 7.0005 | 0.7982 | 99.3 | 100.0 | 13 |
| 11/21 | 119 | FEED | | | | 2.0192 | 0.1187 | 0.3124 | 97.4140 | 0.0618 | 0.0273 | | | |
| 11/21 | 122 | 1C | 255 | 200 | 120 | 1.3909 | 0.1260 | 0.0000 | 94.5051 | 2.6482 | 0.8222 | 35.1 | 100.0 | 13 |
| 11/21 | 125 | 1C | 255 | 200 | 120 | 1.2782 | 0.1048 | 0.0000 | 95.2311 | 2.0102 | 0.9174 | 28.3 | 100.0 | 13 |
| 11/21 | 128 | 1C | 255 | 200 | 120 | 1.2367 | 0.1016 | 0.0000 | 95.2230 | 2.0798 | 0.9246 | 28.4 | 100.0 | 13 |
| 11/29 | 311 | FEED | | | | 1.1916 | 0.0740 | 0.3444 | 98.0411 | 0.0018 | 0.0000 | | | |
| 11/29 | 314 | 1F | 175 | 200 | 120 | 1.5116 | 0.0968 | 0.0035 | 97.0273 | 0.0240 | 1.2122 | 3.0 | 99.2 | 13 |
| 11/29 | 316 | 1F | 175 | 200 | 120 | 1.0318 | 0.0647 | 0.0050 | 97.9539 | 0.0064 | 0.8908 | 1.0 | 98.3 | 13 |
| 11/29 | 319 | 1F | 175 | 200 | 120 | 0.9330 | 0.0572 | 0.0000 | 98.1197 | 0.0043 | 0.8335 | -1.3 | 100.0 | 13 |
| 12/08 | 527 | FEED | | | | 1.6071 | 9.0897 | 0.2837 | 97.9207 | 0.0734 | 0.0000 | | | |
| 12/11 | 602 | 3B | 175 | 200 | 240 | 1.8622 | 0.1045 | 0.0637 | 97.2075 | 0.0000 | 0.5860 | 11.9 | 74.0 | 26 |
| 12/11 | 604 | 3B | 175 | 200 | 240 | 3.8759 | 0.1899 | 0.1181 | 94.9023 | 0.0000 | 0.6776 | -0.9 | 73.5 | 26 |
| 12/11 | 607 | 3B | 175 | 200 | 240 | 3.6310 | 0.1782 | 0.1043 | 95.2655 | 0.0036 | 0.7604 | -0.8 | 75.0 | 26 |
| 12/14 | 678 | FEED | | | | 4.7159 | 0.2332 | 0.5466 | 94.4602 | 0.0000 | 0.0212 | | | |
| 12/15 | 697 | 3D | 150 | 200 | 60 | 3.3410 | 0.1682 | 0.0212 | 95.2781 | 0.0118 | 1.1280 | 1.8 | 94.6 | 6.5 |
| 12/15 | 700 | 3D | 150 | 200 | 60 | 3.5687 | 0.1850 | 0.1253 | 94.8867 | 0.0000 | 1.1810 | 4.6 | 71.1 | 6.5 |
| 12/15 | 703 | 3D | 150 | 200 | 60 | 4.4582 | 0.2274 | 0.2007 | 93.9471 | 0.0000 | 1.0903 | 3.1 | 62.4 | 6.5 |
| 12/20 | 823 | FEED | | | | 2.8100 | 0.1105 | 0.3830 | 96.6221 | 0.0000 | 0.0246 | | | |
| 12/21 | 843 | 3H | 125 | 200 | 30 | 2.7162 | 0.1057 | 0.1862 | 96.4655 | 0.0000 | 0.4471 | -1.1 | 49.2 | 3.25 |
| 12/21 | 847 | 3H | 125 | 200 | 30 | 3.0494 | 0.1202 | 0.2603 | 96.1949 | 0.0000 | 0.3169 | 0.2 | 37.5 | 3.25 |

The invention claimed is:

1. A process for the removal of propylene from a refinery gas stream containing ethylene, propylene, water, carbon oxides, nitrogen compounds and inert alkanes comprising passing the gas stream and a liquid stream containing organic aromatic compounds over a fixed bed of a solid phosphoric acid catalyst and an acid molecular sieve which preferentially reacts the propylene with organic aromatic compounds and absorbs substantially all of said water, carbon oxides and nitrogen compounds and fractionating the effluent from the fixed bed to separate the remaining gas from the liquid stream.

2. The process according to claim 1 wherein there are two of the fixed beds in parallel such that one bed can be used for the reaction while the other bed is being replaced or regenerated.

3. The process according to claim 1 wherein said liquid stream comprises a reformat stream.

(b) feeding the effluent from said reactor to a distillation column wherein gas containing the ethylene and inert alkanes is separated as overheads from a product stream which is taken as bottoms;

(c) feeding the overhead gas from the distillation column and benzene to a distillation column reactor into a feed zone;

(d) concurrently in said distillation column reactor:
  (1) contacting said benzene and said overhead gas stream with a second fixed bed containing an acidic catalytic distillation structure comprising a zeolite catalyst in a distillation reaction zone thereby catalytically reacting at least a portion of said benzene with the ethylene in said overhead gas stream to form ethyl benzene; and
  (2) fractionating the resultant ethyl benzene from unreacted material;

(e) withdrawing the ethyl benzene from the distillation column reactor at a point below said reaction zone; and (f) withdrawing unreacted materials from the distillation column reactor at a point above said reaction zone.

7. The process according to claim 6 wherein said second fixed bed contains a zeolite beta catalyst.

8. The process according to claim 6 wherein the acidic molecular sieve comprises less than 50 wt. % of the alkylation catalysts in the first fixed bed.

9. The process according to claim 8 wherein the solid phosphoric acid and acidic molecular sieve are in separate layers.

10. The process according to claim 8 wherein the solid phosphoric acid and acidic molecular sieve are intimately intermixed.

11. The process according to claim 6 wherein the reformat is heavy reformat.

* * * * *

UNITED STATES PATENT AND TRADEMARK OFFICE
CERTIFICATE OF CORRECTION

Page 1 of 2

PATENT NO. : 5,756,872
DATED : May 26, 1998
INVENTOR(S) : Lawrence A. Smith, Jr. and John R. Adams It is certified that error appears in the above-indentified patent and that said Letters Patent is hereby corrected as shown below:

In the Abstract:
    Line 2 the word reformat should be reformate
    Line 4 the word reformat should be reformate In the Patent:
    Col. 1, line 32 the word reformat should be reformate
    Col. 1, line 60 the word reformat should be reformate
    Col. 2, line 2 the word reformat should be reformate
    Col. 3, line 22 the word reformat should be reformate
    Col. 3, line 24 the word reformat should be reformate
    Col. 3, line 25 the word reformat should be reformate
    Col. 3, line 29 the word reformat should be reformate
    Col. 3, line 30 the word reformat should be reformate
    Col. 3, line 31 the word reformat should be reformate
    Col. 3, line 32 the word reformat should be reformate
    Col. 3, line 33 the word reformat should be reformate

UNITED STATES PATENT AND TRADEMARK OFFICE
CERTIFICATE OF CORRECTION

PATENT NO. : 5,756,872

DATED : May 26, 1998

INVENTOR(S) : Lawrence A. Smith, Jr. and John R. Adams

It is certified that error appears in the above-indentified patent and that said Letters Patent is hereby corrected as shown below:

```
Col. 3, line 44 the word reformat should be reformate
Col. 3, line 50 the word reformat should be reformate
Col. 3, line 61 the word reformat should be reformate
Col. 3, line 63 the word reformat should be reformate
Col. 4, line 3 the word reformat should be reformate
Col. 5, line 67 the word reformat should be reformate
Col. 6, line 2 the word reformat should be reformate
Col. 6, line 9 the word reformat should be reformate
Col. 8, line 7 the word reformat should be reformate
Col. 8, line 8 the word reformat should be reformate
```

Signed and Sealed this

Eighteenth Day of August, 1998

*Attest:*

BRUCE LEHMAN

*Attesting Officer*  *Commissioner of Patents and Trademarks*